United States Patent [19]

Hirano et al.

[11] 4,429,036
[45] Jan. 31, 1984

[54] METHOD OF FORMING A PHOTOGRAPHIC IMAGE

[75] Inventors: Shigeo Hirano; Yoshihiro Takagi, both of Minami-ashigara, Japan

[73] Assignee: Fuji Photo Film Co., Ltd., Kanagawa, Japan

[21] Appl. No.: 480,650

[22] Filed: Mar. 31, 1983

Related U.S. Application Data

[62] Division of Ser. No. 345,501, Feb. 3, 1982.

[30] Foreign Application Priority Data

Feb. 3, 1981 [JP] Japan .................... 56-14564
Feb. 3, 1981 [JP] Japan .................... 56-14565
Feb. 3, 1981 [JP] Japan .................... 56-14567

[51] Int. Cl.³ .................... G03C 5/24; G03F 7/06
[52] U.S. Cl. .................... 430/405; 430/423; 430/566; 430/949; 430/264; 430/267
[58] Field of Search .............. 430/405, 423, 566, 949, 430/264, 267, 963

[56] References Cited

U.S. PATENT DOCUMENTS

| | | | |
|---|---|---|---|
| 3,730,727 | 5/1973 | Olivares et al. | 430/566 |
| 4,269,929 | 5/1981 | Nothnagle | 430/949 |
| 4,332,878 | 6/1982 | Akimura et al. | 430/264 |
| 4,385,108 | 5/1983 | Takagi et al. | 430/264 |

*Primary Examiner*—Mary F. Downey
*Attorney, Agent, or Firm*—Sughrue, Mion, Zinn, Macpeak and Seas

[57] ABSTRACT

A method of forming a photographic image which comprises development processing with an alkaline aqueous activator solution a silver halide photographic light-sensitive material comprising a support having thereon at least one surface latent image type silver halide emulsion layer, and containing in at least one layer selected from a silver halide emulsion layer and another hydrophilic colloid-layer (1) a hydroquinone series developing agent and (2) an acylhydrazine compound represented by formula (I):

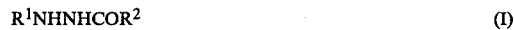

$$R^1NHNHCOR^2 \quad (I)$$

wherein $R^1$ represents an unsubstituted or substituted aryl group or alkyl group; and $R^2$ represents a hydrogen atom, or an unsubstituted or substituted aryl group or alkyl group, wherein the aqueous activator solution or a prebath thereof contains at least one compound represented by formula (II):

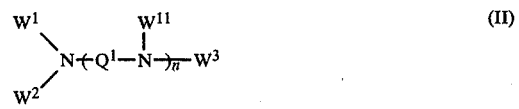

$$\underset{W^2}{\overset{W^1}{\diagdown}}N{+}Q^1{-}\overset{W^{11}}{\overset{|}{N}}{\rightarrow}_{\overline{n}}W^3 \quad (II)$$

wherein each of $W^1$, $W^2$, $W^3$, and $W^{11}$ can represent a hydrogen atom, an unsubstituted or substituted alkyl group, alkenyl group, or alkynyl group, an acyl group, or a sulfonyl group, and $W^1$ and $W^2$, or $W^3$ and $W^{11}$, can be bonded to each other to form a ring; $Q^1$ represents —CH₂CH₂— or —CH₂CH₂CH₂—; and n represents an integer of 1 to 4.

According to this activator type developing method, an image having good quality can be constantly obtained irrespective of the stirring conditions of the processing solution.

18 Claims, No Drawings

METHOD OF FORMING A PHOTOGRAPHIC IMAGE

This is a division of application Ser. No. 345,501, filed Feb. 3, 1982.

BACKGROUND OF THE INVENTION

The present invention relates to a method of forming a photographic image of very high contrast using a silver halide photographic light-sensitive material, and more particularly to a stable activator type developing method which can constantly provide an image having good quality in spite of variations in the stirring conditions of the processing solution.

In printing an original of continuous gradation by use of an offset printing plate or the like, the tone is reproduced by a collection of big and small points called "dots". These dots are very minute and are present in a number of 80 to 200 or more per square inch, and moreover they are required to be sharp individually. In the printing industry, therefore, a combination of a lith type light-sensitive material and a lith developer is employed, which enables formation of a dot image of high contrast by a specific development effect called a "lith effect".

The lith developer is an alkaline solution wherein the concentration of a sulfite acting as a preservative is generally controlled to extremely low levels and only hydroquinone is used as a developing agent. When a lith type light-sensitive material is developed with this solution, the tone of the lith type light-sensitive material is generally higher in contrast with a decrease in the concentration of sulfite ions.

However, since the general properties of the lith type light-sensitive material are greatly influenced by the concentration of the developing agent and are sensitive to changes in the concentration of bromine ions, it is difficult to steadily obtain an image of constant quality. Moreover, because of the very low concentration of sulfite ion as preservative in the lith developer, the lith developer after being prepared is very low in its resistance to oxygen in air and it is disadvantageously easily deteriorated.

Furthermore, in continuously processing the lith type light-sensitive material, the bromine ion is released from an emulsion layer and the developing agent is consumed as is the case with typical silver halide light-sensitive materials. Therefore, even if they are supplemented, it is necessary to check and correct the activity of the developer every several hours. This leads to troublesome or complicated daily production control.

In addition, in processing by such conventional methods, a long development time of from 1 minute to 2 minutes at a development temperature of from 25° C. to 35° C. has been needed to obtain sufficient blackening density and dot quality.

Therefore, methods have eagerly been desired which are able to provide dot images of super high contrast and of good dot quality and screen range.

Japanese Patent Application (OPI) No. 22438/76 (the term "OPI" as used herein refers to a "published unexamined Japanese patent application") discloses a method in which in order to avoid the use of the unstable lith developer, a hydroquinone based developing agent is introduced in a silver halide emulsion and the processing is carried out by use of an alkaline activator in the presence of a hydrazine compound such as hydrazine sulfate to obtain a negative image of high contrast.

This method improves the stability of the processing solution and accelerates the processing rate. This method, however, has the disadvantages that the dot quality obtained is inferior to those of conventional lith type light-sensitive materials, that dot characteristics suitable for use in the plate-making using a contact screen cannot be obtained, and that the screen range is of too high contrast, although contrast characteristics close to those of the lith type light-sensitive material can be obtained. Moreover, for light-sensitive materials in which hydrazine compounds containing an $NH_2NH-$ group have been introduced, it is difficult to hold the contrast characteristics obtained at the beginning of the production of the light-sensitive materials for a long period of time, which is commercially required. This seems due to the vigorous decomposition of the hydrazine compounds with time. Therefore, light-sensitive materials capable of providing images of high contrast cannot be obtained by such a method in which the hydrazine compounds of the type as described above are incorporated in the light-sensitive materials.

U.S. Pat. No. 2,419,975 discloses a method in which a hydrazine compound is added to a silver halide emulsion to obtain a negative image of high contrast. It is described therein that when the hydrazine compound is added to the silver chlorobromide emulsion and the development is carried out using a developer having a pH value as high as 12.8, photographic characteristics of very high contrast, with a $\gamma$ larger than 10, can be obtained. However, many of the hydrazine compounds as disclosed in this patent are of low stability in the light-sensitive materials and cannot be stored for extended periods of time. Also, for strongly alkaline developers having pH values close to 13, developing agents are easily oxidized by air and unstable, and they cannot be stored or used for extended periods of time. Moreover, the development time is nearly equal to those of conventional lith development. Furthermore, for use in the application of plate-making using a contact screen, such images having only the photographic characteristics of high contrast wherein $\gamma$ is 10 or more are inferior in dot quality, are of too high contrast in screen range, and therefore are not sufficiently satisfactory.

Hereinafter, the expressions "dot quality" and "screen range" as used herein will be explained in detail.

The expression "dot quality" means the quality of points when the blackening density is converted through a contact screen in the corresponding point area, and, in general, those having low fringe are preferred.

The expression "screen range" indicates the change of the dot area relative to the amount of exposure. Theoretically it is a characteristic to be determined depending on the density pattern of the contact screen used.

Therefore, even by the methods as described in the above cited references, if a contact screen having a density pattern suitable for a light-sensitive material to be used is chosen and used, a desirable screen range can be obtained. However, such choice of the suitable contact screen according to the type of the light-sensitive material used is undesirably very troublesome for those practically engaged in the operation of the plate-making.

Thus it has long been desired to produce light-sensitive materials which permit the formation of good dots, and which have low fringe, by use of a stable processing solution. Furthermore, it has been desired to produce, practically, the same screen range by use of the same contact screen as would be used in the conventional lith development without employing a special operation such as making of determination of an apporopriate contact screen.

In order to overcome the above-described problems, the inventors have developed a method of rapidly obtaining a negative image of high contrast by processing a silver halide light-sensitive material containing an acylhydrazine compound which is stable in the silver halide light-sensitive material and a hydroquinone based developing agent with an alkaline activator solution, as described in Japanese Patent Application (OPI) Nos. 1936/81 and 9743/81. According to this method, an image of good dot quality and screen range is obtained, but it is desired to further improve dot quality. Furthermore, it has been found that according to such method there is a disadvantage in that the dot quality tends to be changed depending on the condition of stirring during processing.

SUMMARY OF THE INVENTION

Therefore, an object of the present invention is to provide a method of forming a negative image of very high contrast having a gamma ($\gamma$) value of more than 10 by use of a stable processing solution and a stable light-sensitive material.

Another object of the present invention is to provide a method of forming a dot image by use of a stable processing solution and a stable light-sensitive material which permits the dot image having a good dot quality to be formed more rapidly than in the case that a conventional lith developer is used.

Still another object of the present invention is to provide a method of forming a dot image having a dot quality superior to that obtained by the method described in Japanese Patent Application (OPI) Nos. 1936/81 and 9743/81.

A further object of the present invention is to provide a method of forming a dot image in which control of processing solution and operation of processing are simple, and in which the dot quality does not change depending on variations in the operation of processing, particularly variations in the conditions of stirring.

Other objects of the present invention will become apparent from the following detailed description and examples.

These objects of the present invention can be attained by a method of forming a photographic image which comprises development processing with an alkaline aqueous activator solution a silver halide photographic light-sensitive material comprising a support having thereon at least one surface latent image type silver halide emulsion layer, and containing in at least one layer selected from a silver halide emulsion layer and another hydrophilic colloid layer (1) a hydroquinone series developing agent and (2) an acylhydrazine compound represented by formula (I):

wherein $R^1$ represents an unsubstituted or substituted aryl group or alkyl group; and $R^2$ represents a hydrogen atom, or an unsubstituted or substituted aryl group or alkyl group, wherein the aqueous activator solution or a prebath thereof contains at least one compound selected from the group consisting of a compound represented by formula (II), a compound represented by formula (III), and a compound represented by formula (IV):

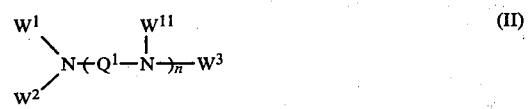

wherein each of $W^1$, $W^2$, $W^3$ and $W^{11}$ can represent a hydrogen atom, an unsubstituted or substituted alkyl group, alkenyl group, or alkynyl group, an acyl group, or a sulfonyl group, and $W^1$ and $W^2$, or $W^3$ and $W^{11}$, can be bonded to each other to form a ring; $Q^1$ represents —CH$_2$CH$_2$— or —CH$_2$CH$_2$CH$_2$—; and n represents an integer of 1 to 4;

wherein each of $W^4$, $W^5$, $W^6$, and $W^7$ can represent an aliphatic group or an aryl group, and $W^4$ and $W^5$, $W^6$ and $W^7$, or $W^5$ and $W^7$ can be bonded to each other to form a ring; and

wherein $Q^2$ represents a sulfur atom or an oxygen atom, each of $W^8$ and $W^9$ can represent an aliphatic group, an aryl group, a heterocyclic group or an amino group, and $W^8$ and $W^9$ can be bonded to each other to form a ring, and $W^{10}$ can represent an aliphatic group or an aryl group, and $W^9$ and $W^{10}$ can be bonded to each other to form a ring.

DETAILED DESCRIPTION OF THE INVENTION

The photographic light-sensitive material which can be used in the present invention is a surface latent image type silver halide photographic light-sensitive material containing in at least one layer selected from a silver halide emulsion layer and another hydrophilic colloid layer a hydroquinone series developing agent and a compound represented by formula (I).

Hereinafter the compounds represented by formula (I) will be explained in greater detail.

In the general formula (I), the aryl group which may be substituted represented by $R^1$ is a mono- or dicyclic aryl group, including benzene and naphthalene rings. Particularly preferred among them is the benzene ring.

The aryl group may be substituted, and examples of preferred substituents include a straight, branched, or cyclic alkyl group preferably containing from 1 to 20 carbon atoms, for example, a methyl group, an ethyl group, an isopropyl group, an n-dodecyl group, etc., an aralkyl group, preferably a mono- or dicyclic aralkyl group having an alkyl moiety containing from 1 to 3 carbon atoms, for example, a benzyl group, etc., an alkoxy group preferably containing from 1 to 20 carbon atoms, for example, a methoxy group, an ethoxy group, etc., a substituted amino group, preferably substituted with an alkyl group containing from 1 to 20 carbon atoms, for example, a dimethylamino group, a diethylamino group, etc., an aliphatic acylamino group preferably having an alkyl group containing from 2 to 21 carbon atoms, for example, an acetylamino group, a heptylamino group, etc., an aromatic acylamino group preferably having a mono- or dicyclic aryl group, for example, a benzoylamino group, etc., or a group represented by the formula X—(Y)ₙ.

In the group represented by the formula X—(Y)ₙ, n represents 0 or 1; Y represents a divalent connecting group, for example, —CONH—, —R¹¹—CONH—, —O—R¹¹—CONH—, —S—R¹¹—CONH—, —R¹¹—, —R¹¹—O—R¹²—, —R¹¹—S—R¹²—, —SO₂NH—, —R¹¹—SO₂NH—, —NHCONH—, —CH₂—CH—N—, —R¹¹—NH—, —R¹¹—O—R¹²—CONH—, —NHCO—R¹¹—, —NHCO—R¹¹—CONH—, —R¹¹—R¹²—, etc., wherein R¹¹ and R¹² (which may be the same or different) each represents a divalent saturated or unsaturated aliphatic group, for example, an ethylene group, a butenylene group, a 1-methylpropylene group, a 1-methylmethylene group, etc., or a divalent aromatic group which may be substituted with a substituent such as an amino group, for example, a phenylene group, a naphthylene group, a 5-amino-1,2-phenylene group, etc. In —R¹¹—R¹²—, R¹¹ and R¹² are different divalent groups.

X represents a group containing (1) a

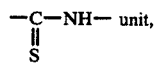

(2) a group containing

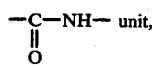

(3) a group represented by

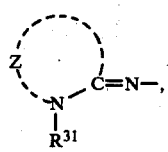

(4) a heterocyclic group, (5) an aralkyl group when n is 1, or (6) an aryl group substituted with an alkyl group.

The heterocyclic group represented by X is a 5-membered or 6-membered ring containing at least one hetero atom which may be condensed with an aromatic ring, particularly a benzene ring, and preferably a monovalent group derived from a heterocyclic compound (for example, a 1,2-benzotriazol-5-yl group, a 5-tetrazolyl group, an indazol-3-yl group, a 1,3-benzimidazol-5-yl group, a hydroxytetraazainden-2- or -3-yl group, etc.), a monovalent group derived from a heterocyclic quaternary ammonium salt (for example, an N-ethylbenzothiazolinium-2-yl group, an N-sulfoethylbenzothiazolinium-2-yl group, an N,N-dimethylbenzimidazolinium-2-yl group, etc.), a monovalent group derived from a heterocyclic compound having a mercapto group (for example, a 2-mercaptobenzothiazol-5- or -6-yl group, a 2-mercaptobenzoxazol-5- or -6-yl group, etc.).

The alkyl group represented by X is a mono- or dicyclic aralkyl group having an alkyl moiety containing 1 to 3 carbon atoms includes, for example, a benzyl group, etc.

The aryl group substituted with an alkyl group represented by X includes, for example, a 2,4-di-tertamyl-1-phenyl group, etc.

The group containing a

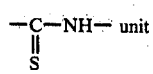

represented by X preferably is an

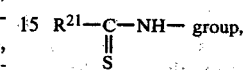

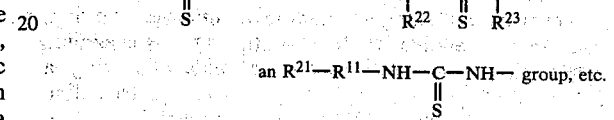

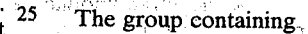

The group containing

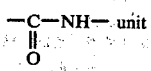

represented by X preferably is an

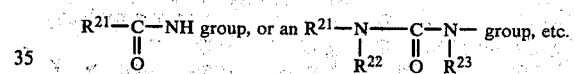

In the above formulae, R²¹ can represent an aliphatic group (for example, an alkyl group, a cycloalkyl group, an alkenyl group, etc.), an aromatic group (for example, a phenyl group, a naphthyl group, etc.), or a heterocyclic group (for example, a thiazolyl group, a benzothiazolyl group, an imidazolyl group, a thiazolinyl group, a pyridinyl group, a tetrazolyl group, etc.); R²² represents a hydrogen atom, an aliphatic group as defined for R²¹ or an aromatic group as defined for R²¹; R²³ can represent a hydrogen atom or an aliphatic group as defined for R²¹; and R¹¹ has the same meaning as defined above, and at least one of R²² and R²³ is a hydrogen atom. R²¹ and R²³ can also be bonded together to form a ring. Preferred examples of the ring include the following:

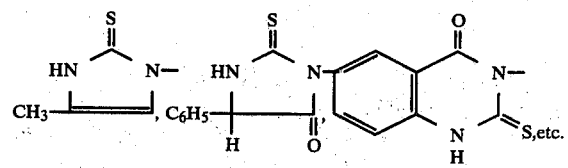

The group represented by R²¹ or R²² may be substituted with an alkoxy group, an alkoxycarbonyl group, an aryl group, an alkyl group, a dialkylamino group, an alkylthio group, a mercapto group, a hydroxy group, a halogen atom, a carboxy group, a nitro group, a cyano group, a sulfonyl group, a carbamoyl group, etc.

In the group represented by the formula

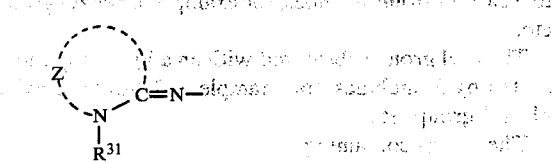

for X, Z represents a group of non-metallic atoms forming together with

a 5-membered or 6-membered heterocyclic ring. Specific examples of the heterocyclic ring include, for example, a thiazoline ring, a benzothiazoline ring, a naphthothiazoline ring, a thiazolidine ring, an oxazoline ring, a benzoxazoline ring, an oxazolidine ring, a selenazoline ring, a benzoselenazoline ring, an imidazoline ring, a benzimidazoline ring, a tetrazoline ring, a triazoline ring, a thiadiazoline ring, a 1,2-dihydropyridine ring, a 1,2-dihydroquinoline ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring, an uracil ring, etc.

$R^{31}$ represents a hydrogen atom or a saturated or unsaturated aliphatic group (for example, an alkyl group, an alkenyl group, an alkynyl group, etc.) which may be substituted with an alkoxy group, an alkylthio group, an acylamino group, an acyloxy group, a mercapto group, a sulfo group, a carboxy group, a hydroxy group, a halogen atom, an amino group, etc.

Of the above-described groups represented by X, particularly preferred groups are the group containing —C—NH— unit,
     ‖
     S the group represented by $R^{21}$—NH—C—NH—
              ‖
              O and the group represented by the formula

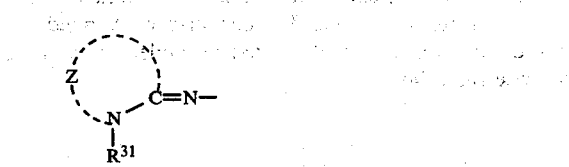

In formula (I), the alkyl group which may be substituted represented by $R^1$ is an alkyl group containing 1 to 10 carbon atoms and which is substituted with a substituent as defined for the aryl group described above.

For a group represented by $R^1$ in formula (I), the aryl group which may be substituted is more preferred than the alkyl group which may be substituted.

In formula (I), the aryl group which may be substituted represented by $R^2$ includes a mono- or dicyclic aryl group, for example, a group containing a benzene ring or a naphthalene ring and, particularly preferred, a benzene ring. The aryl group may be substituted with a substituent, for example, a halogen atom, a cyano group, a carboxy group, a sulfo group, etc. Preferred examples of the aryl group represented by $R^2$ include a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, a 2,5-dichlorophenyl group, etc.

In formula (I), the alkyl group which may be substituted represented by $R^2$ is preferably an alkyl group containing from 1 to 4 carbon atoms, which may be substituted with a substituent, for example, a halogen atom, a cyano group, a carboxy group, a sulfo group, etc. Examples of particularly preferred alkyl groups include a methyl group, an ethyl group, an n-propyl group, an isopropyl group, etc.

Of the compounds represented by the formula (I), those described in Japanese Patent Application (OPI) Nos. 10921/78, 20922/78 and 66732/78, Japanese Patent Application (OPI) Nos. 52050/80 and 90940/80, Japanese Patent Application (OPI) No. 20318/78, Research Disclosure, 17626 (1978, No. 176), etc., are preferred. Particularly preferred compounds are those described in Japanese Patent Application (OPI) Nos. 10921/78, 20922/78 and 66732/78.

Specific examples of the compounds represented by formula (I) are shown below, but the present invention is not limited thereto.

 (I-1)

 (I-2)

 (I-3)

 (I-4)

 (I-5)

 (I-6)

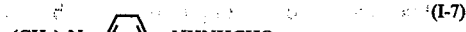 (I-7)

 (I-8)

 (I-9)

 (I-10)

(I-11)

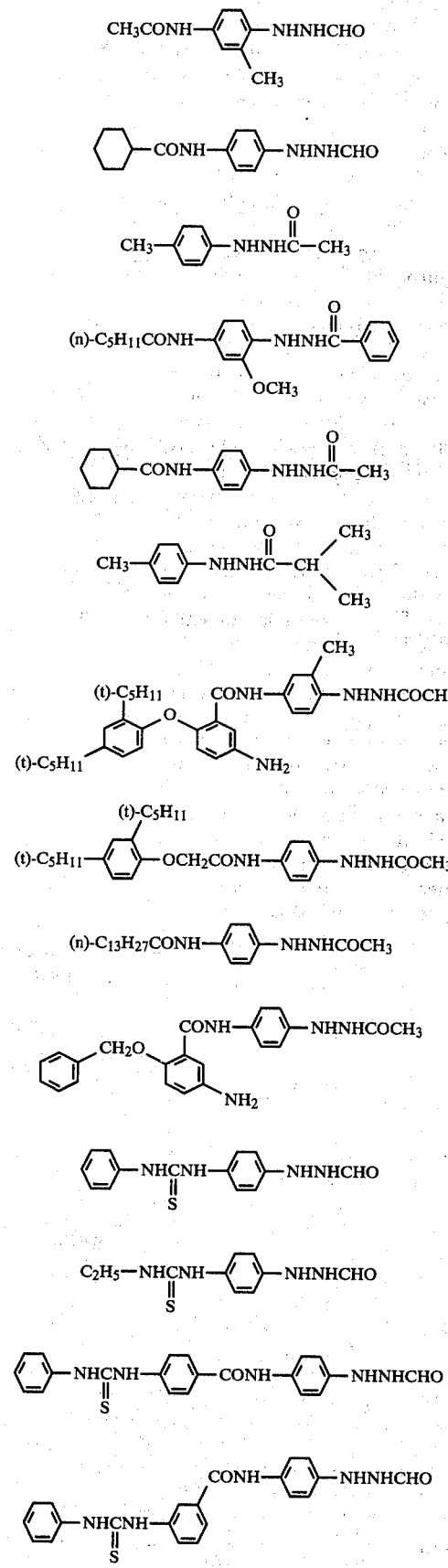
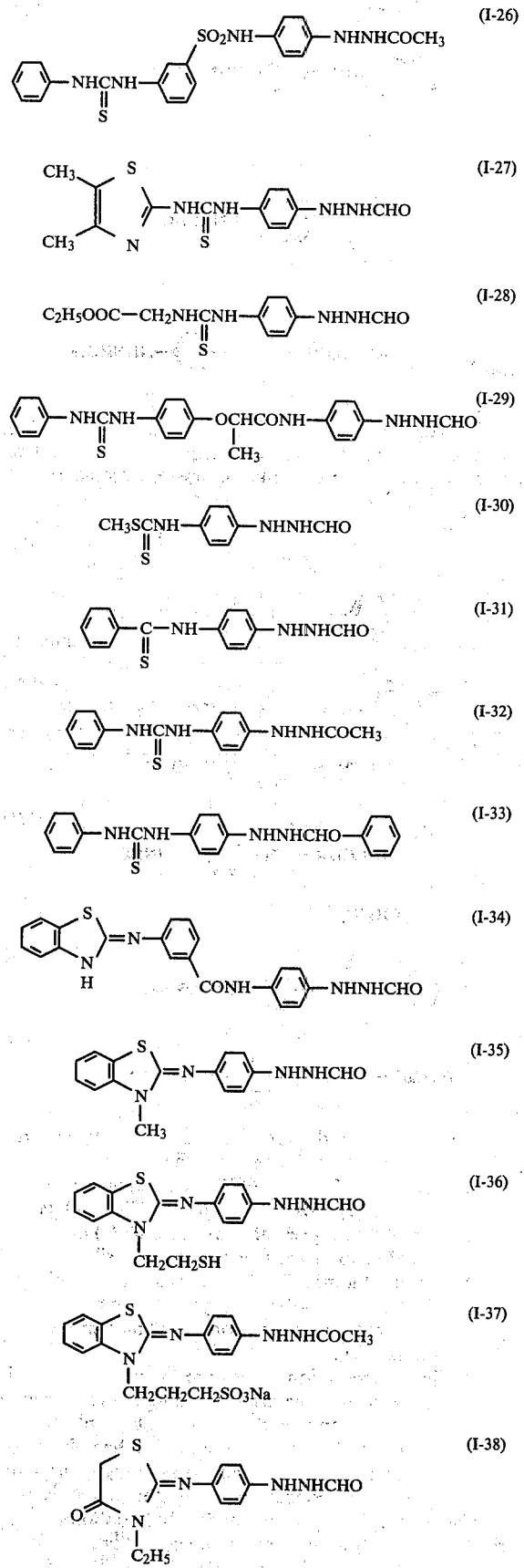

(I-39)
[Structure: 1,3-dimethyl-benzimidazoline =N—C₆H₄—NHNHCHO]

(I-40)
[Structure: HN—C(=S)—N(isobutyl)—C₆H₄—NHNHCHO]

(I-41)
[Structure: benzotriazole—NHCO(CH₂)₂CONH—C₆H₄—NHNHCHO]

(I-42)
[Structure: HS-benzothiazole—NHCOCH₂CH₂—C₆H₄—NHNHCHO]

(I-43)
[Structure: SH-tetrazole—N—C₆H₄—NHC(=S)NH—C₆H₄—NHNHCHO]

(I-44)
[Structure: benzothiazolium-CH₃, CH₂CH=N—C₆H₄—NHNHCHO, PTS⁻]

(I-45)
[Structure: benzothiazolium, CH₂CH₂C(CH₃)—NH—C₆H₄—NHNHCHO, CH₂CH₂SO₃⁻]

(I-46)
[Structure: C₆H₅—NHC(=O)NH—C₆H₄—NHNHCHO]

(I-47)
[Structure: (n)-C₄H₉—NHC(=O)NH—C₆H₄—NHNHCHO]

Synthesis methods for these compounds are described in Japanese Patent Application (OPI) Nos. 10921/78, 20922/78 and 66732/78, Japanese Patent Application (OPI) Nos. 52050/80 and 90940/80, etc.

The compound represented by formula (I) described above is added to at least one layer of a silver halide photographic light-sensitive material in a preferred range of from $10^{-8}$ mol/mol Ag to $10^{-1}$ mol/mol Ag, and particularly preferably from $10^{-6}$ mol/mol Ag to $10^{-2}$ mol/mol Ag.

For the incorporation of the compound of formula (I) in the light-sensitive material, those techniques usually used for the addition of additives to photographic emulsions can be employed. For example, when the compound is water-soluble, it is added as an aqueous solution in a suitable concentration to the photographic emulsion or light-insensitive hydrophilic colloidal solution. On the other hand, when the compound is insoluble or sparingly soluble in water, it is dissolved in a solvent which is selected from organic solvents compatible with water, such as alcohols, glycols, ketones, esters, amides and the like and which exert no adverse influences on the photographic characteristics, and it is added as a solution. In addition, those known methods usually used when water-insoluble (so-called oil-soluble) couplers are added to emulsions in a dispersion form can be employed.

The developing agent for use in the present invention is contained in at least one of the silver halide emulsion layer and other hydrophilic colloidal layers. Developing agents which can be used in the present invention include dihydroxybenzenes such as hydroquinone, chlorohydroquinone, bromohydroquinone, isopropylhydroquinone, methylhydroquinone, 2,3-dichlorohydroquinone, 2,5-dimethylhydroquinone, t-butylhydroquinone, hydroquinone monosulfonate, etc., 3-pyrazolidones such as 1-phenyl-3-pyrazolidone, etc., aminophenols such as N-methyl-p-aminophenol, etc. They can be used alone or in combination with each other. Of these compounds, dihydroxybenzenes are preferred from a practical standpoint, and hydroxyquinones, and specifically hydroquinone are most preferred from a practical standpoint.

The developing agent can be incorporated in the silver halide light-sensitive material by use of hitherto known methods. For example, the developing agent can be dissolved in an organic solvent compatible with water which is selected from alcohols, glycols, ketones, esters, amides and the like, and which exerts no adverse influences on the photographic characteristics. It is then added as a solution to at least one of the silver halide emulsion and a coating solution to form another layer and coated. The method described in Japanese Patent Application (OPI) No. 39928/75 in which a developing agent is added as an oil dispersion to an emulsion can be employed. Moreover, the developing agent can be dissolved in a gelatin solution, added as a gelatin solution, and coated. Furthermore, there can be employed the method described in Japanese Patent Publication No. 15461/70 in which the developing agent is dispersed in alkyl acrylates, alkyl methacrylates, or polymers such as cellulose esters, and the dispersion thus-obtained is added and coated.

The amount of the hydroquinone series developing agent contained in the silver halide light-sensitive material is from 0.1 to 5 mols per mol of silver halide, and preferably from 0.1 to 2 mols per mol of silver halide.

The compound represented by formula (I) and a developing agent may be added to any layer comprising a hydrophilic colloid of the silver halide light-sensitive material, for example, a silver halide emulsion layer, an overcoating layer, a protective layer or other subsidiary layers. The compound represented by formula (I) and a developing agent may be added to different layers or may be added to the same layer.

The silver halide particles as used in the present invention are of the surface latent image type. That is, they are not substantially of the internal latent image type. Specifically, the expression "surface latent image type" as used herein means that where, after from 1 to 1/100 second exposure the development of a photographic light-sensitive material which is prepared by coating on a transparent support conventionally used a silver halide emulsion that does not contain the compound represented by formula (I) used in the present invention, and developing is carried out by a surface development method (A) and an internal development method (B) as described below, the sensitivity obtained by the surface development method (A) is greater than that obtained by the internal development method (B). The sensitivity as herein is defined as follows:

$$S = 100/Eh$$

wherein S is sensitivity, and Eh is an exposure amount required for obtaining a density $\frac{1}{2}(D_{max} + D_{min})$ which is just intermediate between the maximum density ($D_{max}$) and the minimum density ($D_{min}$).

Surface Development Method (A)

A light-sensitive material is developed at 20° C. for 10 minutes by use of a developer having the following formulation:

N-Methyl-p-aminophenol Hemisulfate: 2.5 g
Ascorbic Acid: 10.0 g
Sodium Metaborate Tetrahydrate: 35.0 g
Potassium Bromide: 1.0 g
Water to make: 1 liter Internal Development Method (B)

A light-sensitive material is processed in a bleaching solution containing 3 g/l of potassium ferricyanide and 0.0125 g/l of phenosafranine at about 20° C. for 10 minutes, then washed with water for 10 minutes, and thereafter developed at 20° C. for 10 minutes in a developer having the following formulation:

N-Methyl-p-aminophenol Hemisulfate: 2.5 g
Ascorbic Acid: 10.0 g
Sodium Metaborate Tetrahydrate: 35.0 g
Potassium Bromide: 1.0 g
Sodium Thiosulfate: 3.0 g
Water to make: 1 liter If the emulsion used in the present invention is not of the surface latent image type, not only a negative gradation, but also a positive gradation is formed, and the objects of the present invention cannot be attained.

Silver halide for use in the silver halide light-sensitive material of the present invention includes silver chloride, silver chlorobromide, silver bromide, silver iodobromide, and silver iodochlorobromide.

The average grain size of silver halide particles is preferably not more than 0.7μ and more preferably not more than 0.4μ. The average grain size is a term which is ordinarily used by those in the art of silver halide photography and can easily be understood. By the grain size is meant a grain diameter where the grains are spherical or approximately spherical. Where the grains are cubic, it is calculated from the equation: (an edge length)$\times \sqrt{4/\pi}$. The average is an arithmetical or geometric mean calculated based on projected grain areas. The measurement of the average grain size can be effected by referring, for example, to C. E. K. Mees and T. H. James, *The Theory of The Photographic Process*, 3rd Ed., pp. 36-43, Macmillan Co., (1966).

As a binder or a protective colloid for the photographic emulsion of the light-sensitive material for use in this invention, it is advantageous to use gelatin. Of course, other hydrophilic colloids can be used, including gelatin derivatives, graft polymers of gelatin and other polymers; proteins such as albumin, casein, etc.; cellulose derivatives such as hydroxyethyl cellulose; carboxymethyl cellulose, cellulose sulfate, etc.; various kinds of hydrophilic synthetic high molecular weight compounds, for example, homo- or copolymers such as polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc.

In the photographic light-sensitive material, a chemical sensitizer for a silver halide emulsion, for example, gold, platinum, palladium, iridium, a thiosulfate, etc., a sensitizing dye, for example, a cyanine dye, a merocyanine dye, etc., an anti-irradiation dye, for example, an oxonol dye, a hemioxonol dye, a merocyanine dye, etc., a hardening agent, for example, a chromium salt, an aldehyde, an N-methylol compound, a dioxane derivative, an active vinyl compound (such as 1,3,5-triacryloyl-hexahydro-s-triazine, bis(vinylsulfonyl)methyl ether, etc.), an active halogen compound (such as 2,4-dichloro-6-hydroxy-s-triazine, etc.), etc., can be used. With respect to these compounds, there are described in greater detail in *Research Disclosure*, No. 17643 (December, 1978), and Japanese Patent Application (OPI) Nos. 1936/81 and 9743/81.

The method of forming a photographic image according to the present invention comprises processing the silver halide photographic light-sensitive material described above, after exposure, with an alkaline aqueous activator solution, and is characterized by incorporating into the alkaline activator solution or a prebath thereof which is neutral aqueous solution at least one compound selected from the member consisting of a compound represented by formula (II) described below, a compound represented by formula (III) described below, and a compound represented by formula (IV) described below.

Formula (II) is represented by

wherein each of $W^1$, $W^2$, $W^3$, and $W^{11}$ (which may be the same or different) can represent a hydrogen atom, an unsubstituted or substituted alkyl group, alkenyl group or alkynyl group, an acyl group, or a sulfonyl group, and $W^1$ and $W^2$, or $W^3$ and $W^{11}$, can be bonded to each other to form a ring; $Q^1$ represents —CH$_2$CH$_2$— or —CH$_2$CH$_2$CH$_2$—; and n reprents an integer of 1 to 4.

Formula (III) is represented by

wherein each of $W^4$, $W^5$, $W^6$, and $W^7$ (which may be the same or different) can represent an aliphatic group or an aryl group, and $W^4$ and $W^5$, $W^6$ and $W^7$, or $W^5$ and $W^7$ can be bonded to each other to form a ring.

Formula (IV) is represented by

wherein $Q^2$ represents a sulfur atom or an oxygen atom, each of $W^8$ and $W^9$ (which may be the same or different) can represent an aliphatic group, an aryl group, a heterocyclic group or an amino group, and $W^8$ and $W^9$ can be bonded to each other to form a ring, and $W^{10}$ can represent an aliphatic group or an aryl group, and $W^9$ and $W^{10}$ can be bonded to each other to form a ring.

Hereinafter, the compounds represented by formulae (II), (III) and (IV) will be explained in greater detail.

In formula (II), the alkyl group represented by $W^1$, $W^2$, $W^3$, or $W^{11}$ is preferably an alkyl group containing from 1 to 6 carbon atoms, for example, a methyl group, an ethyl group, an isopropyl group, an n-butyl group, an n-hexyl group, etc. The alkenyl group represented by $W^1$, $W^2$, $W^3$, or $W^{11}$ is preferably an alkenyl group containing from 2 to 6 carbon atoms, for example, an allyl group, etc. The alkynyl group represented by $W^1$, $W^2$, $W^3$, or $W^{11}$ is preferably an alkynyl group containing from 2 to 6 carbon atoms, for example, a propargyl group, etc. These groups may be substituted with one or more substituents. Examples of the substituents include, for example, an alkoxy group (preferably an alkoxy group containing 1 to 3 carbon atoms), a hydroxy group, a carboxy group, a sulfo group, etc. The acyl group represented by $W^1$, $W^2$, $W^3$, or $W^{11}$ is preferably an acyl group containing from 1 to 10 carbon atoms, for example, a formyl group, an acetyl group, a propionyl group, a benzoyl group, etc. The sulfonyl group represented by $W^1$, $W^2$, $W^3$, or $W^{11}$ is preferably a sulfonyl group containing from 1 to 10 carbon atoms, for example, a methanesulfonyl group, an ethanesulfonyl group, a benzenesulfonyl group, etc.

The ring which is formed from $W^1$ and $W^2$, or $W^3$ and $W^{11}$, is preferably a saturated 5-membered or 6-membered ring, for example, a pyrrolidine ring, a perhydropyridine ring, a morpholine ring, etc.

Of the compounds represented by formula (II), those in which $W^1$, $W^2$, $W^3$, and $W^{11}$ each represents a hydrogen atom, an unsubstituted or substituted alkyl group, alkenyl group, or alkynyl group are preferred. Particularly a hydrogen atom, a methyl group, or an ethyl group is preferred, and a hydrogen atom is most preferred for $W^1$, $W^2$, $W^3$, and $W^{11}$.

With respect to $Q^1$, there is no substantial difference between —CH$_2$CH$_2$— and —CH$_2$CH$_2$CH$_2$— in view of the effects obtained.

n represents an integer of 1 to 4, and particularly preferably an integer of 1 or 2.

Specific examples of the compound represented by formula (II) are shown below, but the present invention is not limited thereto.

H$_2$NCH$_2$CH$_2$NH$_2$                               (II-1)
H$_2$N(CH$_2$CH$_2$NH)$_2$H                      (II-2)
H$_2$N(CH$_2$CH$_2$NH)$_3$H                      (II-3)
H$_2$N(CH$_2$CH$_2$NH)$_4$H                      (II-4)

(II-5)

(II-6)

(II-7)

(II-8)

(II-9)

(II-10)

(II-11)

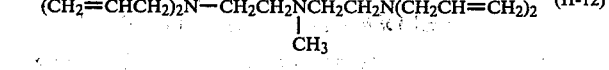
(II-12)

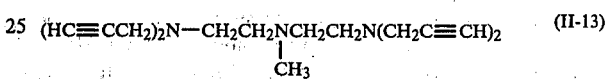
(II-13)

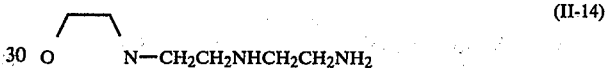
(II-14)

HOCH$_2$CH$_2$NHCH$_2$CH$_2$NH$_2$        (II-15)
HOOCCH$_2$NHCH$_2$CH$_2$NHCH$_2$CH$_2$NH$_2$        (II-16)
HO$_3$SCH$_2$CH$_2$NHCH$_2$CH$_2$NHCH$_2$CH$_2$NH$_2$        (II-17)

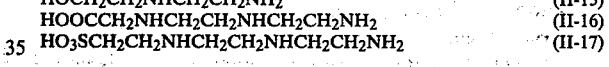
(II-18)

CH$_3$CONHCH$_2$CH$_2$NHCH$_2$CH$_2$NHCOCH$_3$        (II-19)

(II-20)

(HOOCCH$_2$)$_2$NCH$_2$CH$_2$NCH$_2$CH$_2$N(CH$_2$COOH)$_2$        (II-21)
                                CH$_2$COOH

CH$_3$SO$_2$NHCH$_2$CH$_2$NHCH$_2$CH$_2$NHCH$_2$CH$_2$NH$_2$    (II-22)
CH$_3$SO$_2$NHCH$_2$CH$_2$NHCH$_2$CH$_2$NHSO$_2$CH$_3$    (II-23)
H$_2$NCH$_2$CH$_2$CH$_2$NH$_2$    (II-24)
H$_2$NCH$_2$CH$_2$CH$_2$NHCH$_2$CH$_2$NH$_2$    (II-25)
H$_2$NCH$_2$CH$_2$NHCH$_2$CH$_2$CH$_2$NHCH$_2$CH$_2$NH$_2$    (II-26)
H$_2$N(CH$_2$CH$_2$NH)$_5$H    (II-27)
H$_2$NCH$_2$CH$_2$NHCH$_2$CH$_2$CH$_2$NH$_2$    (II-28)
CH$_3$NHCH$_2$CH$_2$CH$_2$NHCH$_2$CH$_2$NH$_2$    (II-29)

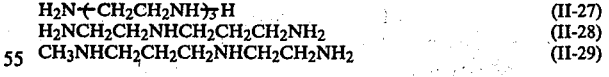
(II-30)

(II-31)

(II-32)

-continued

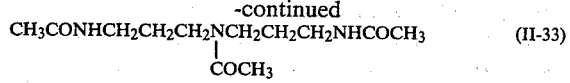  (II-33)

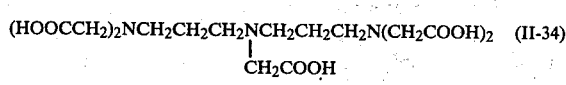  (II-34)

The compounds represented by formula (II) of the present invention are known compounds and can be synthesized by reference to the methods described, for example, in R. B. Wagner and H. D. Zook, *Synthetic Organic Chemistry*, pages 653 to 727, John Wiley and Sons, Inc., New York (1953); and S. R. Sandler and W. Karo, *Organic Functional Group Preparation*, pages 317 to 362, Academic Press, New York (1968).

With respect to polyamine compounds which are particularly preferred for the present invention among the compounds represented by formula (II), synthesis methods are explained more specifically.

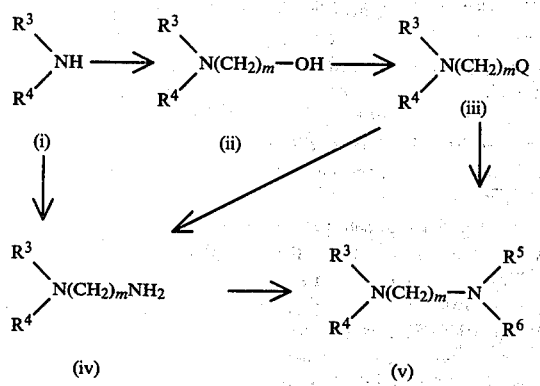

In the above formulae (i) to (v), $R^3$, $R^4$, $R^5$ and $R^6$ each has the same meaning as defined above, m represents 2 or 3, and Q represents Cl or Br.

In order to synthesize a compound represented by the formula (v) in which another amino group is introduced via two or three carbon atoms from an amine derivative represented by the formula (i), the following methods can be employed.

(1) A compound of the formula (i) is converted to a compound of the formula (ii) using an alkylating agent such as ethylene oxide, oxyethane, chlorohydrin, bromohydrin, 3-chloropropanol, etc., in a solvent such as an alcohol, an ether, etc. In such a case when a strong acid such as hydrochloric acid, hydrobromic acid, etc., is subsidiarily formed, an acid removing agent such as pyridine, sodium hydrogencarbonate, etc., may be used.

The compound of the formula (ii) is converted to a halogen derivative of the formula (iii) using thionyl chloride, phosphorus trichloride, phosphorus pentachloride, phosphorus tribromide, phosphorus oxychloride, etc. The compound of the formula (iii) is reacted with an appropriate amine of the formula

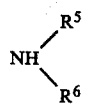

in the presence of pyridine or sodium hydrogencarbonate, etc., to obtain the desired compound of the formula (v).

(2) The compound of the formula (iii) is reacted with ammonia, hexamethylenetetramine, or potassium phthalimide, etc., to prepare a primary amine of the formula (iv). The compound of the formula (iv) is alkylated with $R^5Br$, $R^6OTs$, etc., to obtain the compound of the formula (v).

(3) The compound of the formula (iv) is reacted with a carboxylic acid chloride, a sulfonic acid chloride, an ester of acrylic acid or α-bromoacetic acid, etc., to obtain a compound in which one of $R^5$ and $R^6$ is a hydrogen atom and the other of $R^5$ and $R^6$ is an acyl group, a sulfonyl group, an alkoxycarbonylethyl group or a carboxymethyl group, respectively.

(4) The compound of the formula (iv) can also be synthesized using a reaction of the compound of the formula (i) with ethyleneimine or azetidine.

In formula (III), the aliphatic group represented by $W^4$, $W^5$, $W^6$, or $W^7$ is preferably an alkyl group (which may be substituted) or an alkenyl group (for example, an allyl group, etc.). The aryl group represented by $W^4$, $W^5$, $W^6$, or $W^7$ is preferably a phenyl group (which may be substituted). The total number of the carbon atoms included in $W^4$, $W^5$, $W^6$, and $W^7$ is preferably 30 or less. The ring formed from $W^4$ and $W^5$, $W^6$ and $W^7$, or $W^5$ and $W^7$ is a 5-membered or 6-membered heterocyclic ring, and includes, for example, an imidazolidinethione ring, a piperidine ring, a morpholine ring, etc. The alkyl group described above may be straight chain or branched chain. Examples of the substituents for the alkyl group include, for example, a hydroxy group, a carboxy group, a sulfo group, an amino group, an alkoxy group having an alkyl moiety containing from 1 to 5 carbon atoms, a phenyl group, a 5-membered or 6-membered heterocyclic group (for example, a furyl group, etc.), etc. Examples of the substituents for the aryl group include, for example, a hydroxy group, a carboxy group, a sulfo group, etc.

Of these compounds in which at least three of $W^4$, $W^5$, $W^6$, and $W^7$ are alkyl groups, each alkyl group has from 1 to 5 carbon atoms, and the total number of the carbon atoms included in $W^4$, $W^5$, $W^6$, and $W^7$ is 20 or less are particularly preferred.

Specific examples of the compounds represented by formula (III) are shown below, but the present invention is not limited thereto.

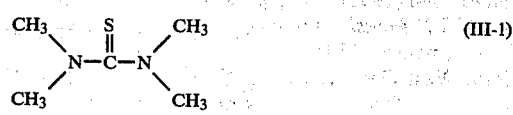  (III-1)

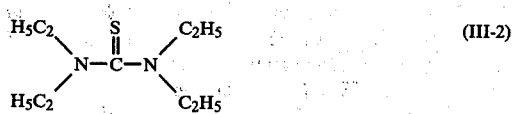  (III-2)

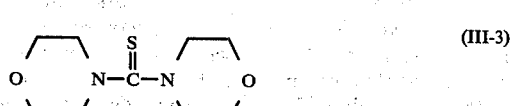  (III-3)

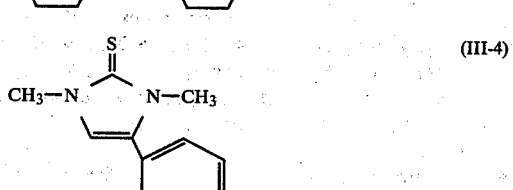  (III-4)

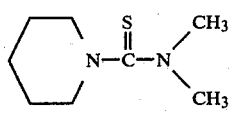 (III-5)

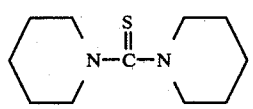 (III-6)

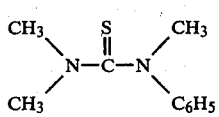 (III-7)

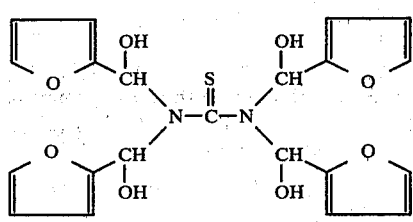 (III-8)

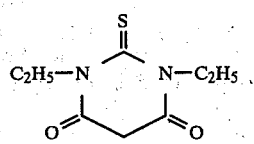 (III-9)

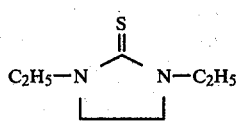 (III-10)

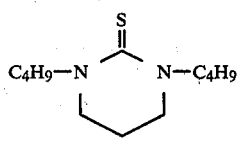 (III-11)

Methods for preparation of these compounds are described, for example, in J. Braun and K. Weizbach, *Berichte der Deutschen chemischen Gesellschaft*, Vol. 63, page 2846 (1930), V. Mozolis and S. Jokubaityte, *Lietuvos T S R Mokslu Akadeurijos Darbai*, Ser. B, Vol. 1969, No. 3, pages 125 to 131, H. Weidinger and H. Eilingsfeld, West German Patent No. 1,119,843, R. A. Donia, *Journal of Organic Chemistry*, Vol. 14, pages 946 to 951 (1949), F. B. Zienty, *Journal of American Chemical Society*, Vol. 68, pages 1388 to 1389 (1946), L. G. S. Brooker, *Journal of American Chemical Society*, Vol. 73, pages 5329 to 5332 (1951), etc.

In formula (IV), $Q^2$ represents a sulfur atom or an oxygen atom. The aliphatic group represented by $W^8$ and $W^9$ is, preferably, for example, an unsubstituted or substituted alkyl group having from 1 to 4 carbon atoms in the alkyl moiety. The substituents for the alkyl group include, for example, a carboxy group, a sulfo group, a hydroxy group, an aryl group (preferably, a phenyl group, etc.), etc. Specific examples of the alkyl groups include, for example, a methyl group, an ethyl group, a propyl group, a butyl group, a carboxymethyl group, a carboxyethyl group, a carboxypropyl group, a sulfoethyl group, a sulfopropyl group, a sulfobutyl group, a hydroxyethyl group, a benzyl group, a phenethyl group, etc. The aryl group represented by $W^8$ or $W^9$ is, preferably, for example, an unsubstituted or substituted aryl group (preferably, a phenyl group, etc.). The substituents for the aryl group include, for example, an alkyl group (preferably, an alkyl group containing from 1 to 4 carbon atoms, etc.), a sulfo group, an alkoxy group (preferably, an alkoxy group containing from 1 to 4 carbon atoms in the alkyl moiety), a halogen atom, etc. Specific examples of the aryl groups include, for example, a phenyl group, a 2-methylphenyl group, a 4-sulfophenyl group, a 4-ethoxyphenyl group, a 4-chlorophenyl group, etc. The heterocyclic group represented by $W^8$ or $W^9$ is, preferably, for example, a 5-membered or 6-membered nitrogen containing heterocyclic group, and more specifically, for example, a 2-pyridyl group, a 3-pyridyl group, a 4-pyridyl group, etc. As the amino group represented by $W^8$ and $W^9$, a substituted amino group is particularly preferred, and includes, for example, an arylamino group (in which the aryl group is preferably an unsubstituted phenyl group or a substituted phenyl group substituted with a substituent, for example, an alkyl group, a sulfo group, a carboxy group, etc.). Specific preferred examples of the amino group includes, for example, a 4-sulfophenylamino group, etc.

The ring formed by bonding $W^8$ and $W^9$ is preferably a 5-membered or 6-membered heterocyclic ring (for example, a piperidine ring, a morpholine ring, a piperazine ring, etc.), etc.

The aliphatic group represented by $W^{10}$ is preferably, for example, an unsubstituted or substituted alkyl group containing 1 to 4 carbon atoms in the alkyl moiety. The substituents for the alkyl group include, for example, a carboxy group, a sulfo group, a hydroxy group, an aryl group (for example, a phenyl group, etc.), etc. Specific examples of the alkyl groups include, for example, a methyl group, an ethyl group, a propyl group, a butyl group, a carboxymethyl group, a carboxyethyl group, a carboxypropyl group, a sulfoethyl group, a sulfopropyl group, a sulfobutyl group, a hydroxyethyl group, a benzyl group, a phenethyl group, etc. The aryl group represented by $W^{10}$ is, preferably, for example, an unsubstituted or substituted aryl group (preferably, a phenyl group). The substituents for the aryl groups include, for example, an alkyl group (preferably, an alkyl group containing 1 to 4 carbon atoms), a sulfo group, an alkoxy group (preferably, an alkoxy group containing from 1 to 4 carbon atoms in the alkyl moiety), a halogen atom, etc. Specific examples of the aryl groups include, for example, a phenyl group, a 2-methylphenyl group, a 4-sulfophenyl group, a 4-ethoxyphenyl group, a 4-chlorophenyl group, etc.

The ring formed by bonding $W^9$ and $W^{10}$ is preferably a 5-membered or 6-membered heterocyclic ring. Of these, a compound represented by formula (IV') described below, in which $W^9$ and $W^{10}$ are bonded each other to form a ring, is more preferred.

 (IV')

In formula (IV'), Z' represents a group of atoms necessary to form a heterocyclic ring (including a heterocyclic ring having at least one ring selected from an unsaturated ring containing 5 to 6 carbon atoms, for example, a benzene ring, a tetrahydrobenzene ring, etc., fused thereto; and $Q^2$ and $W^8$ each has the same meaning as defined in formula (IV) above.

Now, the compounds represented by formula (IV') will be explained in greater detail.

In formula (IV'), $Z'$ represents a group of atoms necessary to form a heterocyclic ring (as a heterocyclic ring itself, preferably a 5-membered ring), for example, a thiazolidine-2-thione ring (for example, a thiazolidine-2-thione ring, a 5-methylthiazolidine-2-thione ring, a 4-carboxythiazolidine-2-thione ring, etc.), a 4-thiazoline-2-thione ring (for example, a 4-methyl-4-thiazoline-2-thione ring, a 4-carboxymethyl-4-thiazoline-2-thione ring, a 4-carboxyl-4-thiazoline-2-thione ring, etc.), a 1,3,4-thiadiazoline-2-thione ring (for example, a 5-ethylthio-1,3,4-thiadiazoline-2-thione ring, etc.), a benzothiazoline-2-thione ring (for example, a benzothiazoline-2-thione ring, a 5-carboxybenzothiazoline-2-thione ring, a 5-sulfobenzothiazoline-2-thione ring, a 5-methylbenzothiazoline-2-thione ring, etc.), a benzoxazoline-2-thione ring (for example, a benzoxazoline-2-thione ring, a 5-sulfobenzoxazoline-2-thione ring, a 5-methylbenzoxazoline-2-thione ring, etc.) or the like.

$W^8$ has the same meaning as defined for $W^8$ in formula (IV).

A cation which is a salt of a sulfo group or a carboxy group each of which is a nuclear substituent on the heterocyclic ring for $W^8$ or $Z'$ is preferably a cation which forms a water-soluble salt. Specifically, an alkali metal atom is preferred, and particularly, $Na^+$ and $K^+$ are preferred.

The nitrogen containing heterocyclic compounds represented by formula (IV') include compounds represented by formulae (IVa) to (IVc) described below. In particular, the compounds represented by the general formula (IVa) are preferred.

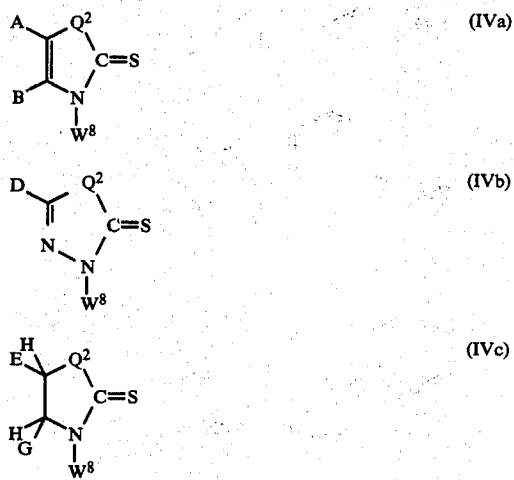

In formulae (IVa), (IVb) and (IVc), $Q^2$ represents a sulfur atom or an oxygen atom, and a sulfur atom is preferred. A and B (which may be the same or different) each represents a hydrogen atom, a carboxy group, an aliphatic group, an aryl group or an alkoxycarbonyl group, or A and B can be bonded to each other and represent a group of atoms necessary to form an unsaturated ring containing 5 to 6 carbon atoms (this ring is preferably substituted with a substituent, for example, a sulfo group, a carboxy group, etc.). When A and B are bonded each other to form an unsaturated ring containing 5 to 6 carbon atoms, the compound represented by formula (IVa) contains at least one group selected from the member consisting of a hydroxy group, a sulfo group and a carboxy group in the molecule thereof. D represents a hydrogen atom, a carboxy group, an aliphatic group or an aryl group. $W^8$ has the same meaning as defined for $W^8$ in formula (IV). Each of E and G (which may be the same or different) represents a hydrogen atom, an aliphatic group or a carboxy group.

Now, the compounds represented by formulae (IVa) to (IVc) will be explained in greater detail.

In formulae (IVa) to (IVc), A and B each represents a hydrogen atom; a sulfo group; a carboxy group; an aliphatic group [for example, an unsubstituted or substituted alkyl group containing from 1 to 6 carbon atoms, preferably from 1 to 4 carbon atoms in the alkyl moiety. The substituents for the alkyl group include, for example, a hydroxy group, a halogen atom, a carboxy group, a sulfo group, an aryl group (preferably a phenyl group, etc.), etc. Specific examples of the alkyl groups include, for example, a methyl group, an ethyl group, a butyl group, a hydroxyethyl group, a sulfopropyl group, a carboxymethyl group, a benzyl group, etc.]; an aryl group [for example, an unsubstituted or substituted aryl group. The substituents for the aryl groups include, for example, an alkyl group, a hydroxy group, a halogen atom, a carboxy group, a sulfo group, etc. Specific examples of the aryl groups include, for example, a phenyl group, a 4-methylphenyl group, a 4-hydroxyphenyl group, a 3- or 4-chlorophenyl group, a 4-carboxyphenyl group, a 4-sulfophenyl group, etc.]; an alkoxycarbonyl group, preferably an alkoxycarbonyl group containing from 1 to 5 carbon atoms in the alkyl moiety, for example, an ethoxycarbonyl group, etc.; or A and B can be bonded to each other and represent a group of atoms necessary to form a ring containing one double bond and 5 to 6 carbon atoms (this ring is preferably substituted with a substituent, for example, a sulfo group, a carboxy group, etc., for example, a trimethylene group, a tetramethylene group, etc., or A and B are bonded to each other and represent a group of atoms necessary to form an unsubstituted or substituted benzene ring. The substituents for the benzene ring include, for example, an alkyl group (preferably an alkyl group containing from 1 to 4 carbon atoms, for example, a methyl group, an ethyl group, etc.), an aryl group (for example, a phenyl group, etc.), an alkoxy group (preferably, an alkoxy group containing from 1 to 4 carbon atoms in the alkyl moiety, for example, a methoxy group, an ethoxy group, etc.), a halogen atom (for example, a chlorine atom, a bromine atom, etc.), an alkyl group substituted with a carboxy group (preferably containing from 1 to 3 carbon atoms in the alkyl moiety, for example, a carboxymethyl group, etc.), an arylamino group (in which the aryl group is preferably a phenyl group, for example, an anilino group, etc.), a carboxy group, a sulfo group, or the like. D represents a hydrogen atom, a carboxy group, an aliphatic group, for example, an unsubstituted or substituted alkyl group containing from 1 to 6 carbon atoms, and preferably from 1 to 4 carbon atoms in the alkyl moiety. The substituents for the alkyl group include, [for example, a hydroxy group, a sulfo group, a carboxy group, etc. Specific examples of the alkyl group include, for example, a methyl group, an ethyl group, a carboxymethyl group, a carboxyethyl group, a hydroxyethyl group, etc.] or an aryl group [for example, an unsubstituted or substituted aryl group (preferably a phenyl group). The substituents for the aryl group include, for example, a sulfo group, a carboxy group, etc. Specific examples of the aryl group include, for example, a phenyl group, a p-sulfophenyl group, etc.]. E and G each represents a hydrogen atom, an aliphatic group [for example, an unsubstituted or substituted alkyl group, and preferably containing from 1 to 4 carbon atoms. The substituents for the alkyl group include, for example, a carboxy group, etc. Specific examples of the alkyl groups include, for example, a methyl group, a carboxymethyl group, a carboxyheptyl group, etc.] or a carboxy group.

Specific examples of the compounds represented by formula (IV) are shown below, but the present invention is not limited thereto.

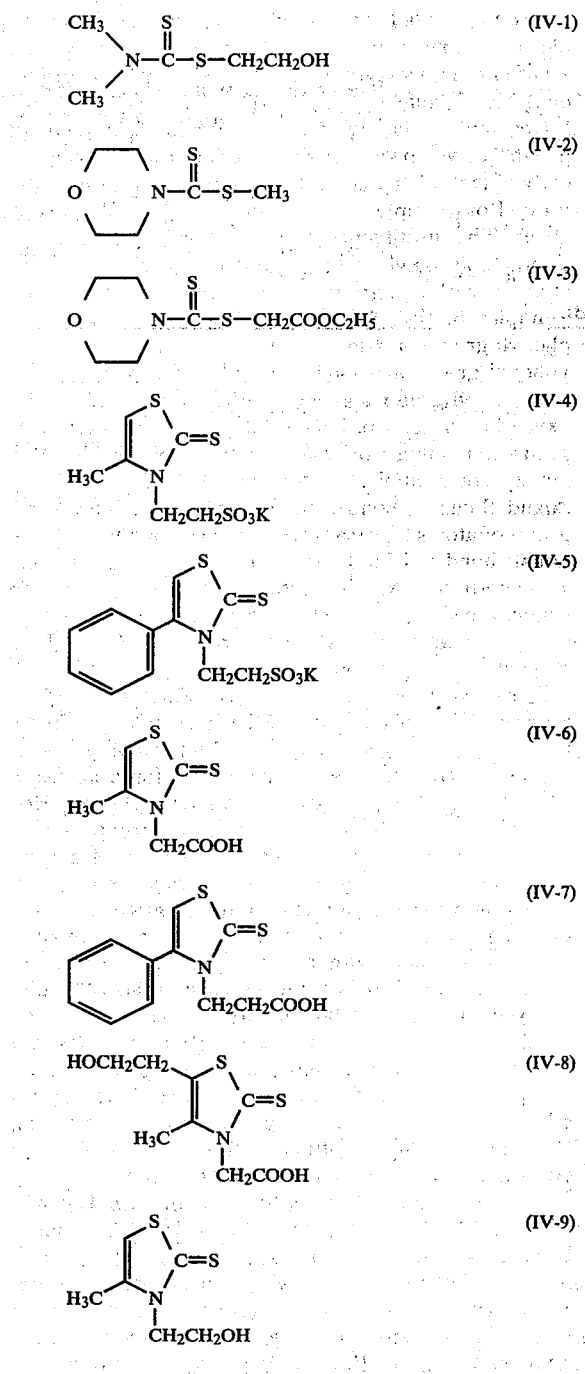
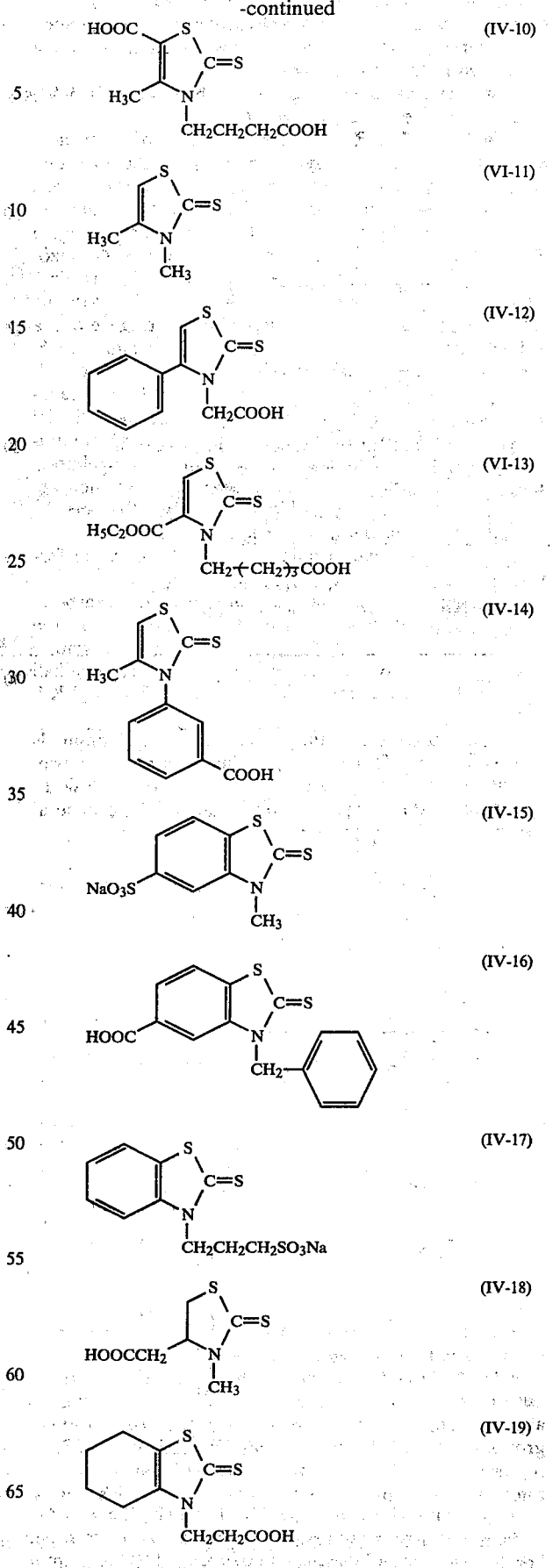

Synthesis examples of the compounds represented by formula (IV) are shown below.

Synthesis of Compound (IV-2)

21.8 g (0.25 mol) of morpholine and 14 g (0.25 mol) of potassium hydroxide were dissolved in 200 ml of alcohol and to the solution, 19 g (0.25 mol) of carbon disulfide was added under cooling (at 5° C. or below) with stirring. After stirring for 2 hours, 35.5 g (0.25 mol) of methyl iodide was added and the mixture was refluxed by heating for 30 minutes. After cooling, the crystals thus deposited were collected by filtration and recrystallized from ethanol to obtain 22 g (yield 50%) of the desired compound. Melting point of the compound was 86° to 87° C.

Synthesis of Compound (IV-4)

To 200 ml of an aqueous solution containing 22.4 g (0.4 mol) of potassium hydroxide, 25 g (0.2 mol) of taurine was dissolved and to the solution, 100 ml of ethanol containing 15.2 g (0.2 mol) of carbon disulfide was added under cooling (at 5° C. or below) with stirring. The mixture was stirred for 2 hours at room temperature to complete the reaction. Then 18.5 g (0.2 mol) of monochloroacetone was added dropwise under cooling (at 5° C. or below) with stirring over about 30 minutes. After reacting at room temperature for 3 hours, the mixture was concentrated and the crystals thus deposited were collected by filtration and dried. The crystals were suspended in ethanol and refluxed by heating for 30 minutes under acidic condition with sulfuric acid (at pH of about 3 to 4). After cooling the crystals thus-deposited were collected by filtration and recrystallized from a diluted aqueous potassium hydroxide solution to obtain 10 g (yield 20%) of the desired compound. Melting point of the compound was above 300° C.

Synthesis of Compound (IV-7)

To 250 ml of a methanol solution containing 44 g (0.5 mol) of β-aminopropionic acid and 28 g (0.5 mol) of potassium hydroxide, was added 30 ml (0.5 mol) of carbon disulfide under cooling (at 5° C. or below) and the mixture was stirred for 2 hours. A methanol solution containing 100 g (0.5 mol) of phenacyl bromide was added dropwise under cooling at 5° C. or below and after the completion of the addition the mixture was stirred at room temperature for 2.5 hours. 220 ml of water was added and the alcohol was distilled off under reduced pressure. The residue was acidified with hydrochloric acid (at pH of about 3 to 4) under cooling with ice with stirring and the crystals thus-deposited were collected and washed with water to obtain 116 g of 4-phenyl-3-(2-carboxyethyl)-4-hydroxythioazolidine-2-thione. Melting point of the compound was 132° C. The crystals were dissolved in 500 ml of glacial acetic acid and refluxed by heating for 30 minutes. After cooling, 1 liter of water was added to the mixture and the crystals thus-deposited were collected by filtration to obtain 89 g (yield 65%) of the desired compound. Melting point of the compound was 134° to 136° C.

Synthesis of Compound (IV-17)

18.1 g (0.1 mol) of 2-methylthiobenzothiazole and 18 g (0.15 mol) of propane sultone were reacted in an oil bath at 130° C. without solvent for 1 hour. After the reaction, 50 ml of xylene was added to the reaction mixture and decanted. Then 50 ml of acetone was added and decanted. 50 ml of water and then an aqueous solution of 28.8 g (0.12 mol) of sodium sulfide were added and the mixture was stirred at room temperature. The crystals thus-deposited were collected by filtration and recrystallized from a 20% water-containing isopropyl alcohol to obtain 10 g (yield 32%) of the desired compound. Melting point of the compound was 312° C. (decomp.).

Other compounds represented by formula (IV) can be synthesized by reference to the above described synthesis examples, and the literature cited below. K. C. Kennard and J. A. Van Allen, *J. Org. Chem.*, Vol. 24, pages 470 to 473 (1959), R. W. Lamon and W. J. Humphlett, *J. Heterocycl. Chem.*, Vol. 4, pages 605 to 609 (1967), M. Ohara, Japanese Patent Publication No. 26203/64, and M. Morita, Yakushi, Vol. 82, pages 36 to 45 (1962).

Of the compounds represented by formulae (II), (III) and (IV), the compounds represented by formula (II) provide particularly remarkable effects.

The amount of the compounds represented by formulae (II), (III) and (IV) to be used varies depending on the particular compound and is not commonly limited. However, for a compound of formula (II), a range of from $10^{-4}$ mol/l to 1 mol/l and particularly from $10^{-3}$ mol/l to $5\times10^{-1}$ mol/l is preferred. With the compounds of formula (III) and the compounds of formula (IV), a range of from 5 mg/l to 15 g/l and particularly from 10 mg/l to 10 g/l is preferred.

The aqueous alkaline activator solution used in the present invention may contain components which are used in conventional lith type developers except for the developing agents themselves. Components which can be incorporated in the activator aqueous solution include, in addition to alkali agents, such as alkali metal hydroxides (e.g., sodium hydroxide, potassium hydroxide), alkali metal carbonates (e.g., sodium carbonate, potassium carbonate, etc.), alkali metal phosphates (e.g., sodium primary phosphate, potassium tertiary phosphate, etc.), alkali metal borates (e.g., sodium borate, sodium metaborate, borax, etc.) and the like, pH buffers, bromides, iodides, antioxidants (e.g., sodium sulfite, potassium metabisulfite, etc.), and the like. Furthermore, if desired, the activator aqueous solution may contain organic solvents (e.g., diethylene glycol, triethylene glycol, diethanolamine, triethanolamine, etc.), water softeners (e.g., sodium tetrapolyphosphate, sodium hexametaphosphate, sodium nitrilotriacetate, ethylenediaminetetraacetic acid or its sodium salt, etc.), hardeners (e.g., glutaraldehyde, etc.), viscosity providing agents (e.g., carboxymethyl cellulose, hydroxyethyl cellulose, etc.), toning agents, surface active agents, deforming agents, and the like. The amounts of these additives to be used can be the same as in conventional aqueous activator solutions and these are well known to one skilled in the art.

The conditions under which the light-sensitive material is processed with the activator aqueous solution of the present invention can be determined properly. While the usual processing temperature is in the range of from 18° C. to 50° C., the processing of the present invention can be carried out at temperatures falling outside this range.

The processing using the activator aqueous solution of the present invention is usually carried out by immersing the light-sensitive material in the activator aqueous solution described above. During this immersion, the activator aqueous solution can be stirred. For this stirring there can be employed various known methods, for example, a method using stirring blades and a method of blowing inert gases thereinto. According to the method of the present invention, the variation of the dot quality can be prevented owing to the change in the state of stirring, such as a change in stirring means, a change in stirring speed, etc.

The imagewise exposure can be carried out in a conventional manner. Also, the imagewise exposure is conducted by the so-called "dot exposure" in which, as in the exposure of conventional lith type light-sensitive material, the original image is exposed through a contact screen. In the method of the present invention, it is not necessary to specially select a contact screen which is suitable to the light-sensitive material to be used, which is different from the conventional substituents for lith type light-sensitive material as described in Japanese Patent Application (OPI) No. 22438/76 and U.S. Pat. No. 2,419,975. Thus, the present invention is advantageous in that by use of the same contact screen as used in the conventional lith type light-sensitive material, equal screen range can be obtained.

In the method of forming dot images according to the present invention, when the processing using the above described activator aqueous solution is carried out in the presence of polyalkylene oxide compounds or their derivatives as described in Japanese Patent Application (OPI) No. 37732/79, much better dot quality can be obtained.

The polyalkylene oxide compounds or derivatives thereof as used in the present invention have average molecular weights of at least 600, and they may be incorporated in the silver halide light-sensitive material or the alkaline activator aqueous solution.

Polyalkylene oxide compounds or derivatives thereof which can be used in the present invention include condensation products of polyalkylene oxides composed of at least 10 units of alkylene oxide containing 2 to 4 carbon atoms (e.g., ethylene oxide, propylene-1,2-oxide, butylene-1,2-oxide, etc., preferably ethylene oxide) and compounds containing at least one active hydrogen atom (e.g., water, aliphatic alcohols, aromatic alcohols, aliphatic acids, organic amines, hexytol derivatives, etc.), and block copolymers of two or more polyalkylene oxides.

Specific examples of such polyalkylene oxide compounds and derivatives thereof are as follows:
Polyalkylene glycols
Polyalkylene glycol alkyl ethers
Polyalkylene glycol aryl ethers
Polyalkylene glycol alkylaryl ethers
Polyalkylene glycol esters
Polyalkylene glycol aliphatic acid amides
Polyalkylene glycol amines
Polyalkylene glycol block copolymers
Polyalkylene glycol graft polymers p Two or more polyalkylene oxide chains may be contained in the molecule. In this case, each polyalkylene oxide chain may be composed of less than 10 alkylene oxide units, but the total alkylene oxide units in the molecule should be at least 10. Where two or more polyalkylene oxide chains are contained in the molecule, they may be composed of different alkylene oxide units, for example, ethylene oxide and propylene oxide. Preferred polyalkylene oxide compounds or derivatives thereof as used in the present invention are those containing from 14 up to 100 of alkylene oxide units.

The polyalkylene oxide compound or derivative thereof is generally added to the silver halide light-sensitive material in an amount ranging from $5 \times 10^{-4}$ g to 5 g per mol of silver halide, and preferably from $1 \times 10^{-3}$ g to 1 g per mol of silver halide. On the other hand, where it is added to the activator aqueous solution, it is generally added in an amount of at least $1 \times 10^{-2}$ g per liter of the activator solution, and preferably in an amount ranging from $5 \times 10^{-2}$ g to 40 g per liter of the activator solution.

Following to the processing with the abovedescribed activator aqueous solution, the light-sensitive material is subjected to fixing processing in a conventional manner.

As a fixing solution, fixing solutions having generally used compositions can be employed. As a fixing agent, an organic sulfur compound which is known to have the function of a fixing agent can be used, as well as a thiosulfate, a thiocyanate, etc. The fixing solution may contain a water-soluble aluminium salt as a hardening agent.

The processing temperature is usually selected in the range of from 18° C. to 50° C., but may be a temperature lower than 18° C. or a temperature higher than 50° C.

In addition to the activator processing and fixing processing described above, processing with other baths (for example, a stopping bath, a hardening bath, etc.) known in a black-and-white processing can be carried out. A period to which the processing with a subsidiary bath is applied and conditions of the processing can be decided in a conventional manner.

According to the method of forming photographic images of the present invention, the following effects which are obtained by processing a light-sensitive material containing a developing agent and the compound represented by the formula (I) with an activator can be attained. That is, the stability of the processing solution can markedly be increased and the control operation of the processing solution can be reduced in comparison with the conventional method wherein the lith type light-sensitive material and the infectious developer are used and furthermore a negative image of extremely high contrast which is equal in dot quality and screen range to that obtained by the conventional method can be obtained in a markedly short period of time. Additionally, in comparison with the method wherein the light-sensitive material to which the known hydrazine compound is added and the developer with a high pH value are used, the stabilities of not only the processing solution but also the light-sensitive material can be improved. Moreover, in comparison with the known method and the method wherein the light-sensitive material to which only hydroquinone is added and the activator to which a hydrazine compound is added are used, there can be obtained a negative image of very high contrast which is markedly excellent in dot quality and screen range. In addition, no special choice of contact screen is required, and by using a contact screen used in the exposure of the usual lith type light-sensitive material, practically the same screen range as in the lith type light-sensitive material can be obtained.

In addition to the above-described effects, by incorporating the compound represented by formula (II), (III) or (IV) into an activator aqueous solution or a prebath thereof, there can be obtained the great advantage that the dot quality is further improved and no variation in dot quality occurs even if the stirring conditions of the activator varies.

The present invention will be explained in greater detail with reference to the following examples, but the present invention is not limited thereto.

EXAMPLE

By adding an aqueous solution of silver nitrate and an aqueous solution of potassium bromide at the same time over a period of 50 minutes to an aqueous solution of gelatin kept at 50° C. while maintaining the pAg at 7.9, a silver bromide emulsion with an average grain size of $0.25\mu$ was produced. After the removal of soluble salts in a conventional manner, sodium thiosulfate was added to the emulsion in the amount of 43 mg per mol of silver bromide and then the silver bromide emulsion was subjected to chemical ripening at 60° C. for 60 minutes.

To the silver bromide emulsion were added hydroquinone dissolved in a 10% aqueous solution of gelatin, 5-methylbenzotriazole as an anti-fogging agent and 3-carboxymethyl-5-[(3-ethyl-2-thiazolidinylidene)ethylidene]rhodanine as a sensitizing dye. Then the resulting mixture was coated on a cellulose triacetate film so that the amount of silver was 40 mg per 100 cm² of the film. This film was designated as Film No. 1. The amount of the hydroquinone coated was 20 mg per 100 cm².

In the same manner as described in the preparation of Film No. 1, 6 film samples were prepared except that Compounds (I-2), (I-22), (I-27), (I-35), (I-43) and (I-46), which are within the scope of formula (I), were added to a coating solution in amounts of $1.0 \times 10^{-3}$ mol, $5.0 \times 10^{-5}$ mol, $4.0 \times 10^{-5}$ mol, $6.0 \times 10^{-5}$ mol, $2 \times 10^{-5}$ mol and $8.0 \times 10^{-4}$ mol per mol of silver halide, respectively. These films were designated as Film Nos. 2 to 7.

By use of a 150 line magenta contact screen, these films were exposed to light through an exposure wedge for sensitometry and thereafter they were developed at 20° C. for 10 seconds with an alkaline activators A1 to A13 having the compositions as described in Table 1 below wherein in one case the activator was stirred and in the other case it was not stirred, stopped, fixed, washed with water and dried to examine their photographic characteristics. The stirring of the activator was carried out by blowing therein a predetermined amount (100 ml/min) of nitrogen during the development through fine openings provided on the side walls of a pipe which had been placed in a one liter activator bath at the bottom thereof.

The results of the dot quality thus-obtained are shown in Table 2. In Table 2, the dot quality was visually evaluated in five grades, in which (1) indicates the best and (5), the worst. As a dot original plate for platemaking, only (1) and (2) are usable, and (3), (4) and (5) are unsatisfactory.

From the results as illustrated in Table 2, it can be seen that the dot quality was maintained constant irrespective of the stirring conditions of the processing, and furthermore it was improved.

TABLE 1

Composition of Activator

| Composition | A1 | A2 | A3 | A4 | A5 | A6 | A7 | A8 | A9 | A10 | A11 | A12 | A13 |
|---|---|---|---|---|---|---|---|---|---|---|---|---|---|
| Sodium Sulfate (anhydrous) | 15 g | 15 g | 15 g | 15 g | 15 g | 15 g | 15 g | 15 g | 15 g | 15 g | 15 g | 15 g | 15 g |
| Sodium Hydroxide | 44 g | 44 g | 44 g | 44 g | 44 g | 44 g | 44 g | 44 g | 44 g | 44 g | 44 g | 44 g | 44 g |
| Potassium Bromide | 7 g | 7 g | 7 g | 7 g | 7 g | 7 g | 7 g | 7 g | 7 g | 7 g | 7 g | 7 g | 7 g |
| Compound II-(1) | — | 1.0 g | — | — | — | — | — | — | — | — | — | — | — |
| Compound II-(2) | — | — | 1.72 g | — | — | — | — | — | — | — | — | — | — |
| Compound II-(3) | — | — | — | 2.30 g | — | — | — | — | — | — | — | — | — |
| Compound II-(5) | — | — | — | — | 1.93 g | — | — | — | — | — | — | — | — |
| Compound II-(8) | — | — | — | — | — | 4.05 g | — | — | — | — | — | — | — |
| Compound II-(10) | — | — | — | — | — | — | 2.13 g | — | — | — | — | — | — |
| Compound II-(24) | — | — | — | — | — | — | — | 1.23 g | — | — | — | — | — |
| Compound II-(27) | — | — | — | — | — | — | — | — | 2.43 g | — | — | — | — |
| Compound III-(1) | — | — | — | — | — | — | — | — | — | 1.0 g | — | — | — |
| Compound III-(2) | — | — | — | — | — | — | — | — | — | — | 1.5 g | — | — |
| Compound IV-(4) | — | — | — | — | — | — | — | — | — | — | — | 1.3 g | — |
| Compound IV-(11) | — | — | — | — | — | — | — | — | — | — | — | — | 1.8 g |
| Water to make | 1 l | 1 l | 1 l | 1 l | 1 l | 1 l | 1 l | 1 l | 1 l | 1 l | 1 l | 1 l | 1 l |

TABLE 2

Dot Quality

| Activator No. | Light-Sensitive Material No. | | | | | | | | | | | | | |
|---|---|---|---|---|---|---|---|---|---|---|---|---|---|---|
| | 1 | | 2 | | 3 | | 4 | | 5 | | 6 | | 7 | |
| | (*1) | (*2) | (*1) | (*2) | (*1) | (*2) | (*1) | (*2) | (*1) | (*2) | (*1) | (*2) | (*1) | (*2) |
| A1 | 5 | 5 | 3 | 4 | 3 | 4 | 3 | 4 | 3 | 4 | 3 | 4 | 3 | 4 |
| A2 | 5 | 5 | 1 | 1 | 1 | 1 | 1 | 1 | 1 | 1 | 1 | 1 | 1 | 1 |
| A3 | 5 | 5 | 1 | 1 | 1 | 1 | 1 | 1 | 1 | 1 | 1 | 1 | 1 | 1 |
| A4 | 5 | 5 | 1 | 1 | 1 | 1 | 1 | 2 | 1 | 2 | 1 | 2 | 1 | 2 |
| A5 | 5 | 5 | 2 | 2 | 2 | 2 | 2 | 2 | 2 | 2 | 2 | 2 | 2 | 2 |
| A6 | 5 | 5 | 2 | 2 | 2 | 2 | 2 | 2 | 2 | 2 | 2 | 2 | 2 | 2 |
| A7 | 5 | 5 | 2 | 2 | 2 | 3 | 2 | 2 | 2 | 2 | 2 | 2 | 2 | 2 |
| A8 | 5 | 5 | 1 | 1 | 1 | 1 | 1 | 1 | 1 | 1 | 1 | 1 | 2 | 2 |
| A9 | 5 | 5 | 2 | 2 | 2 | 2 | 2 | 2 | 2 | 3 | 2 | 2 | 2 | 2 |
| A10 | 5 | 5 | 1 | 2 | 1 | 2 | 1 | 1 | 2 | 1 | 1 | 2 | 1 | 2 |
| A11 | 5 | 5 | 2 | 2-3 | 2 | 2-3 | 2 | 2-3 | 2 | 2-3 | 2 | 2-3 | 2 | 2-3 |
| A12 | 5 | 5 | 1 | 1-2 | 1 | 1-2 | 1 | 1-2 | 1 | 2 | 1 | 1-2 | 1 | 2 |
| A13 | 5 | 5 | 2 | 2-3 | 2 | 2-3 | 2 | 2-3 | 2 | 2-3 | 2 | 2-3 | 2 | 2-3 |

(*1) Without stirring
(*2) With stirring

While the invention has been described in detail and with reference to specific embodiments thereof, it will be apparent to one skilled in the art that various changes and modifications can be made therein without departing from the spirit and scope thereof.

What is claimed is:

1. A method of forming a photographic image which comprises development processing with an alkaline aqueous activator solution an imagewised exposed silver halide photographic light-sensitive material comprising a support having thereon at least one surface latent image type silver halide emulsion layer, and containing in at least one layer selected from a silver halide emulsion layer and another hydrophilic colloid layer (1) a hydroquinone series developing agent and (2) an acylhydrazine compound represented by formula (I):

$$R^1NHNHCOR^2 \quad (I)$$

wherein $R^1$ represents an unsubstituted or substituted aryl group or alkyl group; and $R^2$ represents a hydrogen atom, or an unsubstituted or substituted aryl group or alkyl group, wherein the aqueous activator solution or a prebath thereof contains at least one compound represented by formula (II):

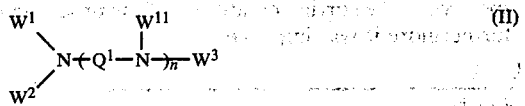

wherein each of $W^1$, $W^2$, $W^3$ and $W^{11}$ can represent a hydrogen atom, an unsubstituted or substituted alkyl group, alkenyl group, or alkynyl group, an acyl group, or a sulfonyl group, and $W^1$ and $W^2$, or $W^3$ and $W^{11}$, can be bonded to each other to form a ring; $Q^1$ represents $-CH_2CH_2-$ or $-CH_2CH_2CH_2-$; and n represents an integer of 1 to 4.

2. A method of forming a photographic image as in claim 1, wherein $R^1$ represents an unsubstituted or substituted phenyl group.

3. A method of forming a photographic image as in claim 1, wherein the amount of the compound represented by formula (I) is from $10^{-8}$ mol/mol Ag to $10^{-1}$ mol/mol Ag.

4. A method of forming a photographic image as in claim 1, wherein the developing agent is a dihydroxybenzene.

5. A method of forming a photographic image as in claim 1, wherein the developing agent is hydroquinone.

6. A method of forming a photographic image as in claim 1, wherein an amount of the developing agent is from 0.1 to 5 mol per mol of silver halide.

7. A method of forming a photographic image as in claim 1, wherein each of $W^1$, $W^2$, $W^3$, and $W^{11}$ represents an alkyl group containing from 1 to 6 carbon atoms, an alkenyl group containing from 2 to 6 carbon atoms, or an alkynyl group containing from 2 to 6 carbon atoms.

8. A method of forming a photographic image as in claim 7, wherein the alkyl group, the alkenyl group, or the alkynyl group is substituted with one or more substituents selected from an alkoxy group containing from 1 to 3 carbon atoms, a hydroxy group, a carboxy group, and a sulfo group.

9. A method of forming a photographic image as in claim 1, wherein each of $W^1$, $W^2$, $W^3$, and $W^{11}$ represents an acyl group containing from 1 to 10 carbon atoms or a sulfonyl group containing from 1 to 10 carbon atoms.

10. A method of forming a photographic image as in claim 1, wherein the ring which is formed by $W^1$ and $W^2$, or $W^3$ and $W^{11}$ is a saturated 5-membered or 6-membered ring.

11. A method of forming a photographic image as in claim 1, wherein each of $W^1$, $W^2$, $W^3$, and $W^{11}$ represents a hydrogen atom, an unsubstituted or substituted alkyl group, an unsubstituted or substituted alkenyl group, or an unsubstituted or substituted alkynyl group.

12. A method of forming a photographic image as in claim 1, wherein the amount of the compound represented by formula (II) is from $10^{-4}$ mol/liter to 1 mol/liter.

13. A method of forming a photographic image as in claim 1, wherein the compound represented by formula (I) is present in a silver halide emulsion layer.

14. A method of forming a photographic image as in claim 1, wherein the compound represented by formula (I) and the developing agent are present in the silver halide emulsion layer.

15. A method of forming a photographic image as in claim 1, wherein the alkaline aqueous activator solution contains at least one compound represented by formula (II).

16. A method of forming a photographic image as in claim 1, wherein the processing is carried out in the presence of a polyalkylene oxide compound or a derivative thereof.

17. A method of forming a photographic image as in claim 16, wherein the polyalkylene oxide compound or the derivative thereof is present in the silver halide light-sensitive material or in the alkaline aqueous activator solution.

18. A method of forming a photographic image as in claim 1, wherein the compound represented by formula (II) is present in the alkaline aqueous activator solution.

* * * * *